US009445588B2

(12) United States Patent
Rath et al.

(10) Patent No.: US 9,445,588 B2
(45) Date of Patent: Sep. 20, 2016

(54) METHODS FOR INCREASING OIL PALM YIELD

(71) Applicant: Valent BioSciences Corporation, Libertyville, IL (US)

(72) Inventors: Andrew Rath, Underwood (AU); Peter D. Petracek, Grayslake, IL (US); Gregory D. Venburg, Deerfield, IL (US); Warren E. Shafer, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 14/641,870

(22) Filed: Mar. 9, 2015

(65) Prior Publication Data

US 2015/0250168 A1 Sep. 10, 2015

Related U.S. Application Data

(60) Provisional application No. 61/950,167, filed on Mar. 9, 2014.

(51) Int. Cl.
*A01N 37/44* (2006.01)

(52) U.S. Cl.
CPC .................................... *A01N 37/44* (2013.01)

(58) Field of Classification Search
CPC ..................................................... A01N 37/44
See application file for complete search history.

(56) References Cited

U.S. PATENT DOCUMENTS

| | | | |
|---|---|---|---|
| 2007/0265166 A1 | 11/2007 | Bardella et al. |
| 2010/0234226 A1 | 9/2010 | Hacker et al. |
| 2010/0323886 A1 | 12/2010 | Voeste et al. |

OTHER PUBLICATIONS

ReTain. Product Details Sheet. [online]. Nufarm, 2012, [retrieved on Jan. 12, 2016]. Retrieved from the Internet: <URL:http://web.archive.org/web/20120325001006/http://www.nufarm.com/NZ/ReTain?printView=true>, 2 pages.*

McFadyen, L. et al., Effects of the Ethylene Inhibitor Aminoethoxyvinylglycine (AVG) on Fruit Abscission and Yield on Pruned and Unpruned Macademia Trees (Abstract), 2012, Scientia Horticulturae, vol. 137, Abstract, 1 page.*

International Search Report and Written Opinion issued Jun. 8, 2015 in corresponding PCT Application No. PCT/US2015/019419.

UNEP Global Environmental Alert Service (GEAS) "Oil palm plantations: threats and opportunities for tropical ecosystems", Dec. 2011.

Chan et al., "Effects of growth regulators on fruit abscission in oil palm, *Elaeis guineensis*" Ann. appl. Biol. (1972), 71, pp. 243-249.

Tranbarger et al., "Regulatory mechanisms underlying oil palm fruit mesocarp maturation, ripening, and functional specialization in lipid and carotenoid metabolism", Plant Physiology, Jun. 2011, vol. 156, pp. 564-584.

Olien et al., "The effect of ethephon-induced gum accumulation in sour cherry (*Prunus cerasus* L.) on shoot water relations and hydraulic conductance", Acta Horticulturae 137, 1983 Growth Regulators, pp. 55-64.

Silverman et al., "Aminoethoxyvinylglycine effects on late-season apple fruit maturation", Plant Growth Regulation 43; 2004, pp. 153-161.

Retamales et al., "AVG and fruit set: a tool for which novel applications are still being developed in various fruit crops—the case of walnuts", Proc XIth IS on Plant Bioregulators in Fruit Porduction Ed.: G. Costa Acta Hort. 884, ISHS 2010, pp. 337-342.

Rath et al., "PalMega plant growth regulator for oil palm. Technical information from the experimental programme", Valent BioSciences Corporation, 2014, pp. 1-12.

Blaak et al., "Breeding and inheritance in the oil palm, (*Elaeis guineensis* Facq.) methods of bunch quality analysis", J. West African Institute of Oil Palm Research, 1963, 4, pp. 146-155.

* cited by examiner

*Primary Examiner* — John Pak
*Assistant Examiner* — Andriae M Holt
(74) *Attorney, Agent, or Firm* — Wood, Phillips, Katz, Clark & Mortimer

(57) ABSTRACT

The present invention is directed to methods of using aminoethoxyvinylglycine (AVG), or a salt thereof, on oil palm before harvest to increase oil production.

5 Claims, No Drawings

METHODS FOR INCREASING OIL PALM YIELD

CROSS-REFERENCE TO RELATED APPLICATION

This application claims priority of U.S. Provisional Application 61/950,167 filed Mar. 9, 2014, the disclosure of which is incorporated herein by reference.

FIELD OF THE INVENTION

The present invention is directed to methods of using aminoethoxyvinylglycine ("AVG", aviglycine) and salts thereof on oil palm prior to harvest to increase oil production.

BACKGROUND OF THE INVENTION

Oil palms (*Elaeis guineensis, Elaeis oleifera*, or a cross thereof) are palms that are grown to produce oil. Oil palms grow up to 20 meters tall. Their fruit is reddish in color and about the size of a plum. The fruits grow in large bunches which grow around the palm. The time from pollination of the flowers to maturation of the fruit is about five to six months. Oil palms produce bunches year-round and the fruits are harvested as they reach maturity.

The oil palm's fruit consists of a fleshy outer layer that surrounds a palm kernel. Oil is extracted from the pulp of the fleshy outer layer and from the kernel. Oil palm is an important crop for vegetable oil production and is grown on about 15 million hectares worldwide (UNEP Global Environmental Alert Service, December 2011). The demand for palm oil is expected to double by 2020.

To meet the increasing demand for palm oil and improve efficiency, agronomic methods such as tree spacing, increased planting, fertilization, and irrigation as well as genetic improvement have been developed to optimize oil production (Corley, R. H. V. and P. B. Tinker, 2003, The Oil Palm, 4$^{th}$ edition, New York, John Wiley and Sons, 590 pp). There is still a need, however, for methods to increase production of currently planted oil palms. There is also still a need to maximize the oil production of plants produced through genetic improvement. Further, there is a need to increase oil production of the palms managed by spacing, increased planting, fertilization, and irrigation.

Ethylene is a two carbon gaseous hydrocarbon molecule that acts as a regulator of plant growth and development. Ethylene plays important roles in many physiological processes through the lifecycle of plants including the promotion of germination, reduction of early plant growth, increase in male flower number, abscission of flowers and fruit, and promotion of ripening (Abeles, F. A., P. W. Morgan and M. E. Saltveit, 1992, Ethylene in Plant Biology, 414 PP).

The effect of ethylene on the oil content of oil palm fruit is not well understood, however, the available literature suggests that application of ethylene increases oil content. For example, Chan, et al. (1972, Ann. Appl. Biol. 71: 243-249) showed that preharvest application of the ethylene-releasing agent ethephon (2-chloroethyl phosphonic acid) to attached bunches of oil palm fruit increased oil content by 7%. Tranbarger, et al. (2011, Plant Physiol. 156: 564-584) found concomitant increase in preharvest oil content and the ethylene level generated endogenously in the oil palm fruit. These reports suggest a relationship between increased ethylene levels and increased palm oil content.

Despite showing promise as a way to increase oil content, ethylene has numerous negative effects on plants which are well known in plant physiology. For example, ethylene promotes abscission of fruits and flowers which would decrease yield and yield potential (Abeles, F. A., P. W. Morgan and M. E. Saltveit, 1992, Ethylene in Plant Biology, 414 pp). In fruit trees and bulbs, ethylene can cause the physiological disease gummosis (Olien, W. C. and M. J. Bukovac, 1983, Acta Hort. 137: 55-64). Gummosis is a generalized disorder of trees in which polysaccharide gum is overproduced, exuded, and deposited on the bark. Gummosis affects water relations, promotes disease, is attractive to wood-boring insects, causes shoot death, and leads to early tree decline. Based on these effects, application (particularly repeated application) of ethylene may not provide an overall benefit in oil palm.

Accordingly, there is a need for practical methods to increase the amount of oil that oil palm trees produce. These methods should produce more oil while not harming the oil palm and should be easy to apply to the fruit or oil palm.

SUMMARY OF THE INVENTION

In one aspect, the invention is directed to methods of increasing the content of oil in oil palm fruits by application of AVG, or a salt thereof, to the oil palm fruit before the oil palm fruit is harvested.

DETAILED DESCRIPTION OF THE INVENTION

AVG ([S]-trans-2-amino-4-(2-aminoethoxy)-3-butenoic acid, aminoethoxyvinylglycine, aviglycine) is a known ethylene antagonist. AVG formulations (such as those available from Valent BioSciences Corporation, Libertyville, Ill.) have been shown to inhibit fruit drop and retain stone fruit and apple fruit quality (Silverman, et al., 2004. Plant Growth Reg. 43:153-161), increase cherry and walnut fruit set (Retamales and Petracek, 2010. Acta Hort. 884:337-341), and increase male flower number in cucurbits.

Applicants unexpectedly found that the AVG increases the oil yield in oil palms when AVG is applied before harvest of the fruit. This finding was unexpected because the literature shows that ethylene increases oil in oil palm when applied before harvest. This suggests that application of the ethylene antagonist AVG would have the opposite effect as ethylene on the oil content of oil palm. Applicants, however, found that the amount of oil increased when AVG was applied before harvest to the fruits.

Applicants also found that the quality of the oil from an AVG salt form treated oil palms was not negatively impacted by the treatments. For example, the oil from the AVG-HCl treated oil palms did not have increased free fatty acid content (A. Rath and V. Shashikant, 2014, "PalMega Plant Growth Regulator for Oil Palm. Technical Information from the Experimental Programme," Example 10, Valent BioSciences Corporation).

In one embodiment, the invention is directed to methods for increasing oil content of oil palm fruit comprising applying an effective amount of AVG, or a salt thereof, to oil palm fruit before the oil palm fruit is harvested.

In a preferred embodiment, a solution of AVG prepared with a formulation of AVG-HCl is applied to the oil palm fruit before the oil palm fruit is harvested.

The timing of application of AVG, or a salt thereof, to the bunches of fruit is after formation of the bunches. This timing does not include when the oil palm is a seedling.

Preferably, the timing range is from initial flowering to prior to harvest. More preferably, the timing range is from just prior to initial fruit drop through early fruit drop from the most mature bunch or bunches on the oil palm. This timing corresponds to about 3 to 4 weeks before harvest to the day of harvest. Most preferably, the timing corresponds to 1 to 2 weeks before harvest to the day of harvest.

Preferably, the concentration of AVG, or a salt thereof, that is applied to the plant is from about 1 to about 10,000 ppm. The more preferred concentration is from about 20 to about 2,000 ppm. The most preferred concentration is from about 100 to about 500 ppm.

Preferably, the volume of the application of AVG, or a salt thereof, is from about 20 to about 2000 ml per palm plant. The most preferred volume of application is from about 100 to about 600 ml per palm plant.

Preferably, the AVG, or a salt thereof, dose is from about 0.02 mg to about 20 g per palm per application. The more preferred AVG, or a salt thereof, dose is from about 0.4 mg to about 4000 mg per palm per application. The most preferred AVG, or a salt thereof, dose is from about 10 mg to about 300 mg per palm per application.

The preferred interval of application is from about every 7 to about every 21 days. The most preferred interval of application is from about every 10 to about every 14 days.

Adjuvants such as surfactants, humectants, stickers, spreaders, urea, oils, and salts may be incorporated in a composition containing AVG to improve performance.

AVG (or a salt thereof), or a composition comprising AVG (or a salt thereof), may be foliar applied to aerial parts of the oil palm including bunches and fronds by methods such as backpack sprayers, mist blowers, extended wand sprayers, tractor or ATV-mounted or UTV-mounted sprayers or aerial application by fixed wing, helicopter, or drone aircraft. The most preferred foliar application is targeted to the oldest bunches of fruits on the palm. AVG (or a salt thereof), or a composition comprising AVG (or a salt thereof), may be applied to the ground by drip irrigation or fertigation with nutrients or applied by trunk or bunch injection.

As used herein, "yield" refers to the amount of oil that is produced from the oil palm.

As used herein, "prior to harvest," "before harvest," and "preharvest" all refer to a time before the most mature bunches and their fruits are harvested from the oil palm.

Throughout the application, the singular forms "a," "an," and "the" include plural reference unless the context clearly dictates otherwise.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

These representative embodiments are in no way limiting and are described solely to illustrate some aspects of the invention.

The invention is demonstrated by following representative examples. The following examples are offered by way of illustration only and not by way of limitation.

EXAMPLES

Example 1

Plant material: A field study was executed in a plantation in Malaysia to compare the effects of repeat bunch-directed applications of AVG to the untreated control (UTC). In this study, AVG was provided in a formulation as AVG-HCl at a concentration of 20% w/wt. For both treatments, 148 palms per block with 4 rows per block covering about 1.1 hectare were used. The bi-clonal DxP palms were 3 to 4 years old.

Treatment application: A motorized mist blower was used to apply AVG (500 ppm, at 600 mL/palm or 300 mg/palm/application) to the lower and most mature rows of bunches of each palm.

The time required for 360 degree spray application around each palm was about 30 seconds. Sprays were applied every 10 days which coincided with harvest frequency in this block. Treatments were applied from September to November 2013.

Harvest: Harvest picks occurred every 10 days. Bunches were harvested at the point of initial fruit drop. At harvest, UTC bunches had lost an average of 34.8 fruit/bunch and the AVG-treated bunches had lost 33.9 fruits/bunch. Bunch weight results were recorded over six harvests picks for the 10 representative palms that were tagged for each treatment.

Oil content: At each harvest pick beginning with the fourth harvest pick interval, bunches were selected and individually bagged, tagged, and transferred to the laboratory for determination of oil content. Bunch samples from each harvest were analyzed in the laboratory for oil content using standard methods (Blaak, et al., 1963, J. West African Institute of Oil Palm Research, 4:146-155).

Results: Effects on oil content and bunch weight of repeat preharvest application of AVG on oil palm are found in Table 1.

Oil content: Oil content of oil palm fruit surprisingly increased 2.7% by whole-palm preharvest application of AVG compared to the UTC (Table 1). Oil content was 0.284 oil wt/bunch wt for the AVG treatment and 0.277 oil wt/bunch wt for the UTC.

Bunch weight: Oil palm bunch weight increased 8.3% by whole-palm preharvest application of AVG compared to the UTC (Table 1). Bunch weight was 10.02 kg/bunch for the AVG treatment and 9.25 kg/bunch for the UTC.

Oil yield: Oil yield was determined as kg oil/bunch=oil content*bunch wt. Oil yield increased 11.2% by preharvest application of AVG compared to the UTC (Table 1). Oil yield was 2.85 kg/bunch for the AVG treatment and 2.56 kg/bunch for the UTC. The results in Table 1 show that repeated application of AVG on oil palm increased oil content and resulted in increased oil yield.

TABLE 1

Effects on oil content and bunch weight of repeat preharvest application of AVG on oil palm.

| Treatment | Average Oil Content (oil wt/bunch wt) | Average Bunch Weight (kg/bunch) | Oil Yield (kg oil/bunch) |
|---|---|---|---|
| UTC | 0.277 | 9.25 | 2.56 |
| AVG | 0.284 | 10.02 | 2.85 |
| Percent difference (AVG/UTC) | +2.7% | +8.3% | +11.2% |

Example 2

Plant material: A second field study was executed in a plantation in Malaysia to compare the effects of repeat broadcast directed bunch applications of AVG to the untreated control (UTC). For both treatments, 148 palms per block with 4 rows per block covering about 1.1 ha were used. The bi-clonal DxP palms were 3 to 4 years old.

Treatment application: A motorized mist blower was used to apply AVG (500 ppm at 600 mL/plant or 300 mg/palm/application) to the lower and most mature rows of bunches of each palm plant. The time required for 360 degree spray application per palm plant was about 30 seconds. Treatments were applied every 20 days and harvests of treated palms were 10 days after treatments. Untreated bunches were harvested every 10 days. Treatments were applied from September to November 2013.

Results: Effects on oil content and bunch weight of repeat preharvest application of AVG on oil palm in the second field study are found in Table 2.

Oil content: Oil content of oil palm fruit surprisingly increased 4.5% by preharvest application of AVG compared to the UTC (Table 2). Oil content was 0.299 oil wt/bunch wt for the AVG treatment and 0.286 oil wt/bunch wt for the UTC.

Bunch weight: Oil palm bunch weight increased 6.6% by whole-palm preharvest application of AVG compared to the UTC (Table 2). Bunch weight was 9.36 kg/bunch for the AVG treatment and 8.78 kg/bunch for the UTC.

Oil yield: Oil yield was determined as kg oil/bunch=oil content*bunch wt. Oil yield was increased 11.6% by whole-palm preharvest application of AVG compared to the UTC (Table 2). Oil yield was 2.80 kg/bunch for the AVG treatment and 2.51 kg/bunch for the UTC. The results in Table 2 show that repeated application of AVG on oil palm increased oil content and resulted in increased oil yield.

TABLE 2

Effects on oil content and bunch weight of alternating 20-day repeat preharvest sprays of AVG, and harvests of oil palm

| Treatment | Average Oil Content (oil wt/bunch wt) | Average Bunch Weight (kg/bunch) | Oil Yield (kg oil/bunch) |
|---|---|---|---|
| UTC | 0.286 | 8.78 | 2.51 |
| AVG | 0.299 | 9.36 | 2.80 |
| Percent difference (AVG/UTC) | +4.5% | +6.6% | +11.6% |

The invention claimed is:

1. A method of increasing oil content of oil palm fruit comprising applying an effective amount of aminoethoxyvinylglycine (AVG), or a salt thereof, to oil palm fruit before the oil palm fruit is harvested, wherein the effective amount is from about 10 mg to about 300 mg AVG per palm per application.

2. The method of claim 1 wherein the salt is AVG-HCl.

3. The method of claim 1 wherein the AVG, or a salt thereof, is applied from about three weeks before the fruit is harvested to about the day before the fruit is harvested.

4. The method of claim 1 wherein the AVG is applied from about every 7 to about 21 days.

5. The method of claim 4 wherein the AVG is applied from about every 10 to about 14 days.

* * * * *